US006958484B2

(12) United States Patent
Mitrovic

(10) Patent No.: US 6,958,484 B2
(45) Date of Patent: Oct. 25, 2005

(54) METHOD AND APPARATUS FOR 2-D SPATIALLY RESOLVED OPTICAL EMISSION AND ABSORPTION SPECTROSCOPY

(75) Inventor: Andrej S. Mitrovic, Phoenix, AZ (US)

(73) Assignee: Tokyo Electron Limited, Tokyo (JP)

( * ) Notice: Subject to any disclaimer, the term of this patent is extended or adjusted under 35 U.S.C. 154(b) by 315 days.

(21) Appl. No.: 10/432,713

(22) PCT Filed: Nov. 28, 2001

(86) PCT No.: PCT/US01/43164

§ 371 (c)(1),
(2), (4) Date: May 27, 2003

(87) PCT Pub. No.: WO02/44674

PCT Pub. Date: Jun. 6, 2002

(65) Prior Publication Data

US 2004/0026035 A1 Feb. 12, 2004

Related U.S. Application Data

(60) Provisional application No. 60/253,139, filed on Nov. 28, 2000.

(51) Int. Cl.[7] ............................................. G01N 21/86
(52) U.S. Cl. ................................... 250/559.27; 250/216
(58) Field of Search ......................... 250/559.27, 221, 250/216, 228, 554; 356/72, 338, 339; 216/67, 59, 60

(56) References Cited

U.S. PATENT DOCUMENTS

| | | | |
|---|---|---|---|
| 5,014,217 A | 5/1991 | Savage | |
| 5,347,460 A | 9/1994 | Gifford et al. | |
| 5,450,205 A | 9/1995 | Sawin et al. | |
| 5,751,416 A | 5/1998 | Singh et al. | |
| 5,980,767 A | 11/1999 | Koshimizu et al. | |
| 6,090,302 A | 7/2000 | Smith, Jr. et al. | |
| 6,132,577 A | 10/2000 | Smith, Jr. et al. | |
| 6,815,653 B2 * | 11/2004 | Tsay et al. | 250/206 |

* cited by examiner

Primary Examiner—Que T. Le
(74) Attorney, Agent, or Firm—Oblon, Spivak, McClelland, Maier & Neustadt, P.C.

(57) ABSTRACT

A multi-point detection method and system for analyzing a composition within an examination area. The system simultaneously acquires multi-dimensional distributions (e.g., two- or three-dimensional distributions) of plasma optical emissions at at least two wavelengths. Such diagnostics are useful for real-time spatially-resolved measurements of plasma electron temperature distributions and/or chemical species concentrations within a plasma processing chamber (50). Generally, the system analyzes/diagnoses the measurement of line-of-sight light emission or absorption in the plasma.

8 Claims, 3 Drawing Sheets

METHOD AND APPARATUS FOR 2-D SPATIALLY RESOLVED OPTICAL EMISSION AND ABSORPTION SPECTROSCOPY

CROSS-REFERENCE TO RELATED APPLICATIONS

This application is a National Stage of International Application No. PCT/US01/43164 filed Nov. 28, 2001, which claims the benefit of U.S. Provisional Application No. 60/253,139 filed Nov. 28, 2000.

BACKGROUND OF THE INVENTION

1. Field of the Invention

The present invention is directed to a method and apparatus for resolving optical emissions and absorptions, and more particularly to a method and apparatus for resolving optical emissions and absorptions in at least two dimensions.

2. Discussion of the Background

Recently, the use of optical diagnostics in plasma processing tools has seen a significant increase. Optical diagnostics provide the benefits of real-time signal acquisition along with being inherently non-intrusive. Known systems using optical diagnostics, such as optical emission spectroscopy, acquire signals from only a single line of sight in space at a time, typically via an optical fiber feed. At one end, light emitted from the plasma passes through a small aperture (or iris) located outside an optical vacuum window and it is focussed onto one end of the optical fiber via a focusing lens. The opposite end of the optical fiber is generally optically connected to the input of a spectrometer, wherein the light spectrum may be dispersed via a grating and the incremental wavelength spectrum recorded using a photo-detector. In such a system, acquiring a signal from another line of sight in space requires repositioning of the optical system, meaning that the measurement at the next point in space is not done at the same time as for the previous line(s) of sight.

Other known optical systems use multiple fixed optical fiber feeds. The use of multiple feeds allows the estimation of the variation, at the same instant of time, of the measured property within some region of the plasma, but such systems do not support full multi-dimensional distributions of measured plasma properties since they suffer from the "one optical fiber channel per measurement line of sight" limitation. Moreover, such systems also suffer from the fact that the optical emission or absorption they intend to measure is, in actuality, the integrated light emitted or absorbed along the line of sight which falls within the field of view of the optical apparatus.

One method and device for detecting the end point of a plasma process is disclosed in U.S. Pat. No. 5,980,767 (hereinafter "the '767 patent"), assigned to the assignee of the present invention. FIG. 1 of the '767 patent is reproduced as FIG. 1 of the present application. In that figure, a single detector 22 is used to analyze the condition of the plasma.

SUMMARY OF THE INVENTION

It is an object of the present invention to provide a multi-point detection method and system for analyzing a composition within an examination area. This object, and other advantages of the present invention, are addressed by a system that simultaneously acquires multi-dimensional distributions (e.g., two- or three-dimensional distributions) of plasma optical emissions at at least two wavelengths. Such diagnostics are useful for real-time spatially-resolved measurements of plasma electron temperature distributions and/or chemical species concentrations within a plasma processing chamber. Generally, the system analyzes/diagnoses the measurement of line-of-sight light emission or absorption in the plasma.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENT

Figure 1:
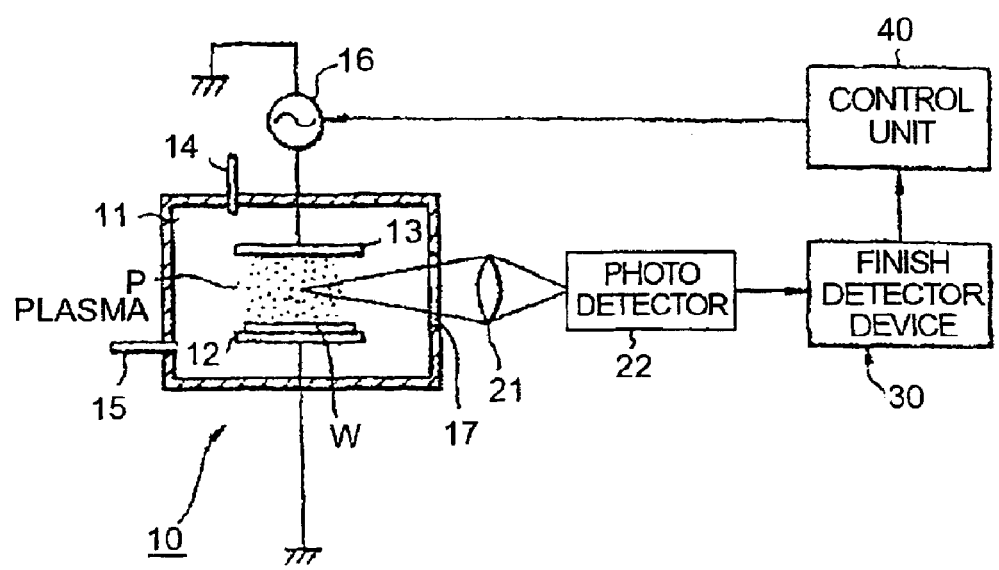
FIG. 1 is a schematic illustration of an optical end point detector system as described in a known system.
Figure 2:
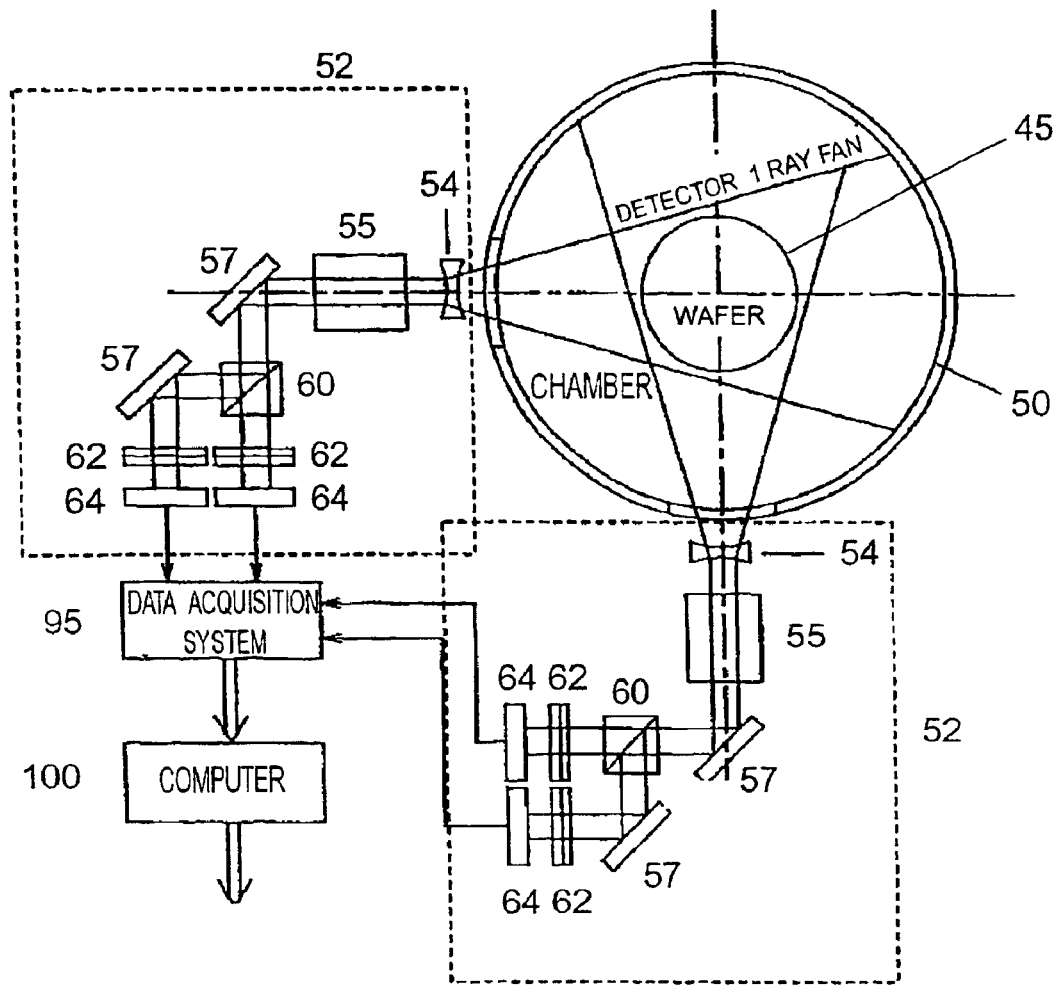
FIG. 2 is a schematic illustration of a multi-detector system according to the present invention.

Referring now to the drawings, wherein like reference numerals designate identical or corresponding parts throughout the several views, FIG. 2 is a schematic illustration of one embodiment of the present invention used to collect information about the processing conditions of a wafer 45 within a chamber 50. At least two detectors 52 are located circumferentially outside the processing chamber 50 such that light passes through corresponding viewports. Each detector 52 has a viewing angle $\Theta$ (e.g. the angle of the "fan of light rays" seen by the detector). Light emitted from the chamber 50 is passed through a focusing lens 54 and an optical system 55 such that the incoming light rays are projected onto a beam splitter 60 by way of reflectors 57 (e.g., mirrors). The beam splitters 60 separate the light rays into two beams, each of which is passed through an optical filter 62 of adequate bandpass, set at the wavelength whose intensity needs to be monitored. Many different devices can be used as optical filters, e.g. colored glass and thin-film coated filters, etc. The two filtered beams are then sent onto a line-CCD device array 64, which is used to measure their light intensities. The optical system is designed in such a way that each pixel readout on the line-CCD corresponds to the light intensity at the desired wavelength of an incoming light ray on the detector, one of many rays in the "ray fan". Acquisition of light intensities on all CCD arrays, for all wavelengths and in all detectors can be made simultaneous with appropriate trigger/electronic shutter circuitry. Those intensities are passed to a data acquisition system 95, which passes the acquired data to a computer 100. (In an alternate embodiment, data can be provided to the computer 100 directly from the CCDs 64.)

In general, with a minimum of two detectors, and once a set of intensity profiles has been read from all CCDs, a numerical procedure called "tomographic inversion" (also known as "Abel inversion") can be used to recover the full two-dimensional distributions of light emission, at the two wavelengths, in a region of the plasma where the "ray fans" of the set of detectors intersect. The application of tomographic inversion (or Abel inversion) to such a set of data is discussed in detail in Gabor Herman's monographs "Image Reconstruction from Projections: The Fundamentals of Computerized Tomography" and "Image Reconstruction from Projections: Implementation and Applications", and they are herein incorporated by reference in their entirety. These two-dimensional distributions can then be used to obtain plasma properties of interest. The measurements are simultaneous on all detectors, and thus a "snapshot in time" is obtained of the plasma property distribution of interest. With the use of appropriate (e.g. fast, electronically shuttering) CCDs, suitable triggering/shutter control electronics, and large buffer memories for measurement storage, one can acquire plasma property distributions in rapid succession, which allows the study of time-evolving phenomena in the plasma, such as chemical species concentrations.

In an alternate embodiment, the system provides multi-wavelength acquisition without a speed/repetition rate penalty. Such an embodiment splits the beam into plural channels with filters and line-CCD detectors. Although acquisition can be done on two wavelengths, additional wavelengths can also be monitored. For example, by adding "n" additional splitters and "n" additional filters (where n>=1) and by using another CCD (or another part or parts of a multi-frequency CCD), an (n+2)-wavelength detector can be provided. The same software that handled the first two wavelengths would then take care of the additional n wavelengths.

Such a system can be extended to three dimensions by adding additional planes of detection (e.g., above or below the plane formed by the detector array fan shown in FIG. 2). Using three dimensions, the changes in the plasma can be analyzed across volumes of the plasma.

Figure 3:
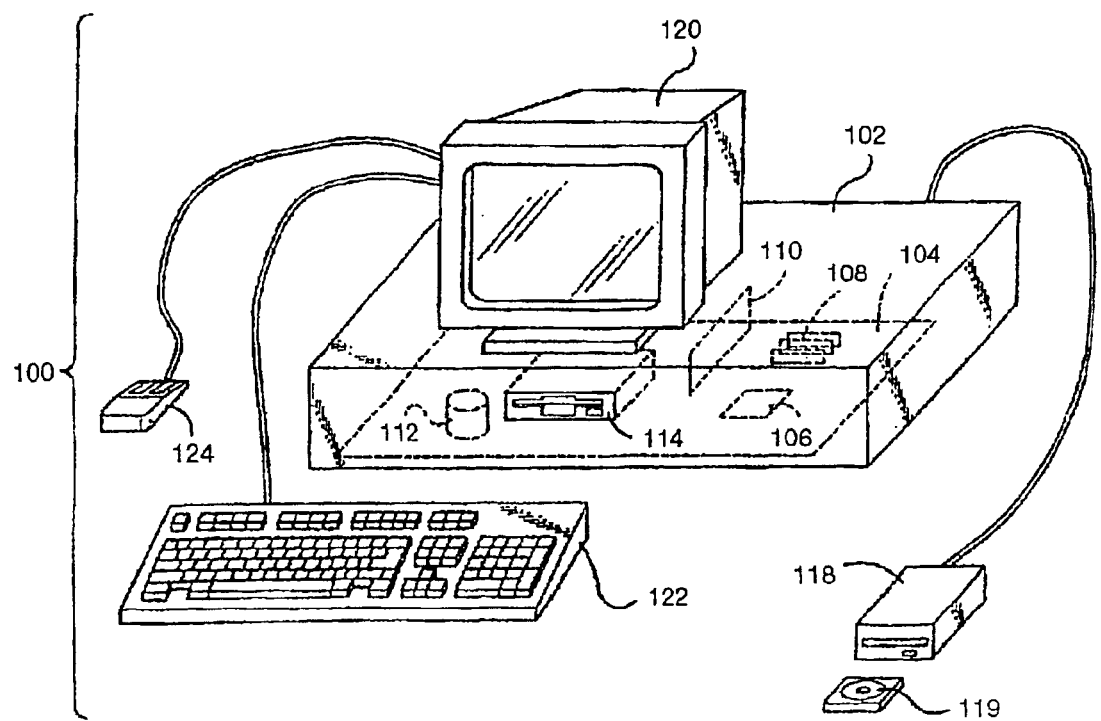
FIG. 3 is a schematic illustration of a computer for analyzing the sampled emission and/or absorption data according to the present invention.

Referring now to the drawings, wherein like reference numerals designate identical or corresponding parts throughout the several views, FIG. 3 is a schematic illustration of a computer system for measuring two-dimensional distributions of light emissions. A computer 100 implements the method of the present invention, wherein the computer housing 102 houses a motherboard 104 which contains a CPU 106, memory 108 (e.g., DRAM, ROM, EPROM, EEPROM, SRAM, SDRAM, and Flash RAM), and other optional special purpose logic devices (e.g., ASICs) or configurable logic devices (e.g., GAL and reprogramable FPGA). The computer 100 also includes plural input devices, (e.g., a keyboard 122 and mouse 124), and a display card 110 for controlling monitor 120. In addition, the computer system 100 further includes a floppy disk drive 114; other removable media devices (e.g., compact disc 119, tape, and removable magneto-optical media (not shown)); and a hard disk 112, or other fixed, high density media drives, connected using an appropriate device bus (e.g., a SCSI bus, an Enhanced IDE bus, or a Ultra DMA bus). Also connected to the same device bus or another device bus, the computer 100 may additionally include a compact disc reader 118, a compact disc reader/writer unit (not shown) or a compact disc jukebox (not shown). Although compact disc 119 is shown in a CD caddy, the compact disc 119 can be inserted directly into CD-ROM drives which do not require caddies. In addition, a printer (not shown) also provides printed listings of two-dimensional distributions of light emissions.

As stated above, the system includes at least one computer readable medium. Examples of computer readable media are compact discs 119, hard disks 112, floppy disks, tape, magneto-optical disks, PROMs (EPROM, EEPROM, Flash EPROM), DRAM, SRAM, SDRAM, etc. Stored on any one or on a combination of computer readable media, the present invention includes software for controlling both the hardware of the computer 100 and for enabling the computer 100 to interact with a human user. Such software may include, but is not limited to, device drivers, operating systems and user applications, such as development tools. Such computer readable media further includes the computer program product of the present invention for calculating two-dimensional distributions of light emissions. The computer code devices of the present invention can be any interpreted or executable code mechanism, including but not limited to scripts, interpreters, dynamic link libraries, Java classes, and complete executable programs.

Obviously, numerous modifications and variations of the present invention are possible in light of the above teachings. It is therefore to be understood that, within the scope of the appended claims, the invention may be practiced otherwise than as specifically described herein.

What is claimed is:

1. In a plasma processing chamber for processing substrates, wherein the processing chamber includes plural optical viewports, the improvement comprising:
   a first optical system for receiving a first series of light beams in a first direction;
   a first detector for receiving the first series of light beams from the first optical system;
   a second optical system for receiving a second series of light beams in a second direction;
   a second detector for receiving the second series of light beams from the second optical system; and
   a calculator for calculating two-dimensional distributions of light emissions from substantially simultaneous outputs of the first and second detectors, wherein at least a portion of the first and second series of light beams pass across a common area within the plasma processing chamber.

2. The improvement as claimed in claim 1, wherein the first and second directions are substantially perpendicular.

3. The improvement as claimed in claim 1, wherein the first and second optical systems comprise at least one beam splitter.

4. The improvement as claimed in claim 1, wherein the first and second detectors comprise multi-frequency detectors.

5. The improvement as claimed in claim 1, wherein the first and second detectors comprise CCDs.

6. The improvement as claimed in claim 1, wherein the first and second optical systems comprise at least one filter interposed between the plasma processing chamber and the first and second detectors.

7. The improvement as claimed in claim 1, wherein the substrate comprises a wafer.

8. The improvement as claimed in claim 1, wherein the calculator for calculating two-dimensional distributions of light emissions comprises a computer.

* * * * *